United States Patent [19]

Pettersson et al.

[11] Patent Number: 5,772,875

[45] Date of Patent: Jun. 30, 1998

[54] CHROMATOGRAPHY COLUMN

[75] Inventors: Conny Pettersson, Hässelby; Ingrid Porrvik, Upsala; Eva Eriksson, Stockholm, all of Sweden

[73] Assignee: Amersham Pharmacia Biotech AB, Upsala, Sweden

[21] Appl. No.: 750,329

[22] PCT Filed: Jun. 2, 1995

[86] PCT No.: PCT/SE95/00632

§ 371 Date: Mar. 4, 1997

§ 102(e) Date: Mar. 4, 1997

[87] PCT Pub. No.: WO95/34359

PCT Pub. Date: Dec. 21, 1995

[30] Foreign Application Priority Data

Jun. 14, 1994 [SE] Sweden .................................. 9402091

[51] Int. Cl.$^6$ .................................................. B01D 15/08
[52] U.S. Cl. .................................. 210/198.2; 210/502.1; 210/635; 210/656
[58] Field of Search .................................. 210/635, 656, 210/198.2, 502.1; 95/88, 85; 96/101, 105, 107

[56] References Cited

U.S. PATENT DOCUMENTS

| | | |
|---|---|---|
| 3,682,315 | 8/1972 | Hallee .................................. 210/198.2 |
| 3,796,657 | 3/1974 | Pretorius .............................. 210/198.2 |
| 3,808,125 | 4/1974 | Good .................................... 210/198.2 |
| 3,878,092 | 4/1975 | Fuller ................................... 210/198.2 |
| 4,557,830 | 12/1985 | Onitsuka ............................. 210/198.2 |
| 4,582,608 | 4/1986 | Ritacco ................................ 210/198.2 |
| 4,587,014 | 5/1986 | America ............................... 210/198.2 |
| 4,591,442 | 5/1986 | Andrews .............................. 210/198.2 |
| 4,732,687 | 3/1988 | Muller .................................. 210/198.2 |
| 4,793,920 | 12/1988 | Cortes .................................. 210/198.2 |
| 5,316,680 | 5/1994 | Frechet ................................. 210/635 |
| 5,334,310 | 8/1994 | Frechet ................................. 210/198.2 |
| 5,431,807 | 7/1995 | Frechet ................................. 210/198.2 |
| 5,453,185 | 9/1995 | Frechet ................................. 210/198.2 |
| 5,522,994 | 6/1996 | Frechet ................................. 210/635 |

FOREIGN PATENT DOCUMENTS 161493  11/1985  European Pat. Off. ............ 210/198.2

*Primary Examiner*—Ernest G. Therkorn
*Attorney, Agent, or Firm*—Dinsmore & Shohl LLP

[57] ABSTRACT

A liquid chromatography column including a chromatographic matrix, liquid flow inlet means and liquid flow outlet means, and a distributor located adjacent the inlet and functioning to distribute the incoming liquid. The column includes a matrix is that is monolithic and porous; and in that when eluant passes through the matrix a liquid accommodating gap which is devoid of matrix material is present between the matrix and the distributor.

10 Claims, 1 Drawing Sheet

CHROMATOGRAPHY COLUMN

TECHNICAL FIELD

The present invention relates to a column for liquid chromatography.

DESCRIPTION OF THE PRIOR ART

In liquid chromatography on a porous matrix, a liquid in which a compound is dissolved is allowed to pass the matrix with the compound passing through one or more adsorption/desorption stages in the matrix.

Liquid chromatography matrices normally consist of particles (e.g. beads) which are packed to form a bed in a column tube. The bed is normally held in place in the tube with the aid of two adaptors (plates) which each cover a respective end of the bed and therewith also the cross-sectional area of the column tube. One of the adaptors will normally include an inlet for eluant which prior to penetrating the bed passes through a distributor or spreader which distributes the flow of eluant uniformly over the end-area of the bed. The distributor may have a more or less sophisticated construction. Typical distributors are filter papers, plates/discs in which a large number of holes are disposed uniformly across the plate/disc. In some cases, there is used a central inlet from which there extends a system of passageways which function to distribute the liquid to the distributing holes in the plate.

In order to minimize diffusion and zone broadening during a chromatographic process, the distributor plate is placed in abutment with the inlet area of the matrix bed. This eliminates the risk of particles swirling up from the bed. One drawback with packed chromatography beds is that the beds readily subside such as to form cracks, particularly in conjunction with changes in the rate of flow of the eluant, or when the matrix dries out.

An alternative to matrix beds which consist in packed particles is found in the so-called continuous matrices (also called monolithic matrices) which have been porous. This type of matrix does not tend to form channels as a result of subsidence or settling of the bed. By continuous (monolithic) matrices is meant matrices which are intrinsically coherent. Matrices which consist of packed membranes or filters are not monolithic.

PROBLEMS ENCOUNTERED WITH THE KNOWN TECHNIQUE

It has been found that when conventional distribution techniques are applied to continuous matrices, it is difficult to achieve uniform penetration of the eluant across the end-area of the matrix. The eluant readily penetrates the matrix in the vicinity of the distribution holes but scarcely spreads to those parts of the matrix which lie between said holes. This results in mutually parallel, channel-like flows in the matrix and to a low matrix efficiency, which in turn results in low numbers of theoretical plates or low elution volumes ($V_e$) and also in unfavourable symmetry factors (symmetry factors at 10% of the peak height and defined so that the highest symmetry factor corresponds to 1). The problem is most accentuated in matrices which produce low counter-pressures, i.e. macro-porous matrices of large pore volumes and large pores.

THE INVENTION

It has now been found that the number of theoretical plates, elution volumes and symmetry factors can be improved by providing a liquid gap between the matrix and the distributor during the chromatography process. The positive effect thus achieved is because when the liquid penetrates into the matrix, there is created a continuous layer across the matrix end-area.

The inventive liquid chromatography column is constructed from a column tube which includes a chromatography matrix and a distributor or spreader placed adjacent the inlet and functioning to distribute the incoming liquid. The column is characterized in that the matrix is monolithic and porous and in that as the liquid passes through the matrix, there is present between the matrix and the distributor a gap which does not contain matrix material. The remainder of the column may be of known design. The width of the gap is such as to impart improved properties to the column with respect to number of theoretical plates, symmetry factors and elution volumes in comparison with the case when the distributor plate abuts the matrix.

Our experimental results (see Table 1) show that the number of theoretical plates, elution volumes, peak widths and symmetry factors are functions of gap width, and that the chromatographic optimal values for respective functions need not necessarily be achieved with a common gap width. According to the invention, it is advantageous for the gap width to be such that the number of theoretical plates will lie within ±50% of the maximum value that can be achieved with variation of the gap width. Correspondingly, in accordance with the present invention, the gap width should be adjusted so that the elution volume lies within 80–100% of the total liquid content of the matrix. The symmetry factor should be optimized with the aid of the gap width in relation to the symmetry factor obtained when the gap width is zero, i.e. when the distributor lies flush with the matrix. Symmetry factors that can be achieved by varying the gap width are often 0.5–5, preferably 0.5–3.

In practice, the above general guidelines for achieving optimal chromatographic conditions can normally be attained when the gap width is <2 mm, such as <1 mm and >0.005 mm.

No gap is required in zero liquid flow conditions, but can arise as a result of compression of the monolithic matrix by the liquid flow. In practice, it is preferable that the gap is created when producing the column, when the inlet adaptor and associated distributor or spreader is moved towards the matrix inlet area. In this regard, we have found it very suitable to adapt the width of the gap so that it is always discernible to the eye.

DESCRIPTION OF THE PREFERRED EMBODIMENTS

Figures 1A, 1B:
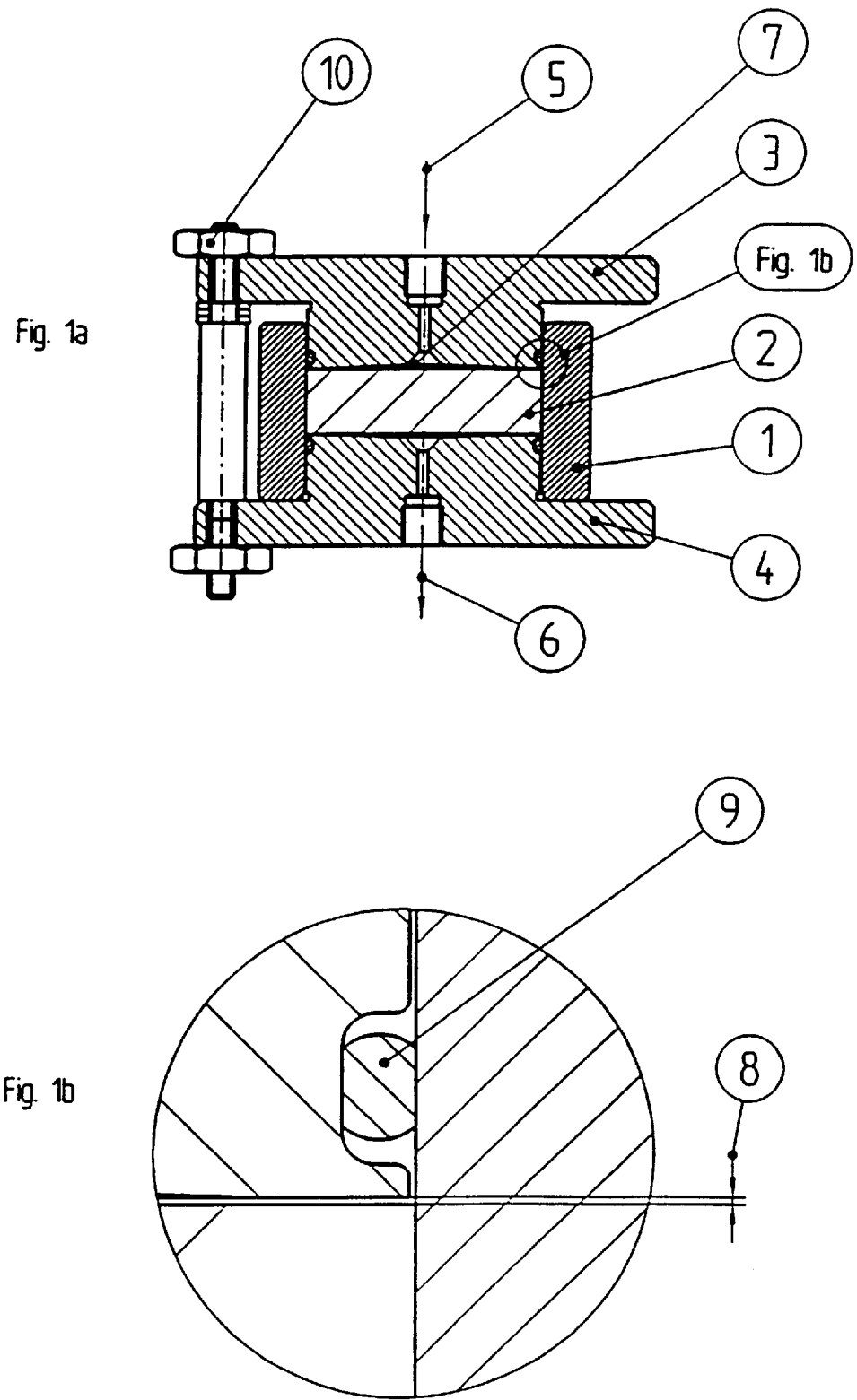
FIG. 1A shows an embodiment of the inventive column into which a flow of liquid is introduced.
FIG. 1B shows an enlarged view of a section of FIG. 1A showing a matrix-free gap.

The distributor will preferably be sufficiently rigid to withstand the pressure of the liquid flow and not flex or bulge outwards towards the matrix.

FIG. 1a illustrates an embodiment of an inventive column into which a flow of liquid is introduced. The column tube (1) is filled with a continuous matrix (2) and the inlet area and outlet area of the matrix are covered by a respective adaptor (3 and 4). The adaptor (3) covering the inlet area is provided with a liquid flow inlet (5) while the adaptor covering the outlet area of the matrix is provided with a liquid flow outlet (6). The liquid flows in the arrowed directions. The inlet adaptor (3) includes a distribution function or facility (7), preferably in the form of a distribution cone. A matrix-free gap (8) is located between the matrix inlet area and the abutment surface of the inlet adaptor (3). The surface of the inlet adaptor proximal to the matrix may conveniently be bevelled from the centre of the adaptor and out towards the periphery thereof, so as to improve distribution of the incoming liquid and minimize the dead volume. The adaptors (3, 4) each include sealing elements (9), for instance in the form of O-rings, which seal against the inner surface of the column tube. The upper adaptor includes means (10) which enable the adaptor to be raised and lowered in relation to the upper surface of the matrix. In the case of the illustrated embodiment, the means (10) has the form of a setting screw.

FIG. 1*b* is an enlarged view of FIG. 1*a*, with the same reference signs as those used in FIG. 1*a*.

Monolithic matrices can be produced in different ways, for instance by the polymerization of inverse emulsions where the oil phase includes polymerizable monomers, or by bulk-polymerization together with a so-called porogen (a solvent which can be washed out after polymerization).

The requirement of a gap in accordance with the invention is determined by the counterpressure exerted by a continuous matrix on the liquid flow to be used in a chromatographic process. Discounting pore sizes and rates of flow, this generally means that the counterpressure radially across the matrix shall be smaller than the counterpressure axially of the matrix (in the flow direction).

Normally, relevant matrices will have a large pore volume (>2 cm$^3$/g, preferably 5–30 cm$^3$/g (measured as a dry matrix of given volume)) in combination with throughflow pores that have a smallest diameter of 0.05 $\mu$m or larger.

The inventive column may include a number of monolithic chromatographic matrices stacked one upon the other.

According to the invention, the chromatographic process is carried out by eluting the contents of the column with a liquid flow with which the counterpressure exerted radially across the matrix will be smaller than the counterpressure exerted axially of the matrix (in the flow direction).

EXPERIMENTAL SECTION

Material and Methods

The matrix used in this experiment was a continuous matrix produced by polymerizing styrene/divinyl benzene in an inverse emulsion in accordance with DE 1160616 and EP 60318. The matrix was placed in a column tube (diameter 35 mm). The matrix had a height of 10 mm and its diameter was adapted to the diameter of the tube, so as to obtain sealing engagement of the matrix with the inner surface of the tube. The column was equipped with a raisable and lowerable adaptor fitted with an eluant distributor. The adaptor functioned to raise/lower the distribution plate relative to the end-area of the matrix when twisted.

The chromatographic system used was a FPLC system with UV detectors (Pharmacia Biotech AB, Uppsala, Sweden).

The rate of flow was 300 cm/h=48 ml/min.
The sample was 10% (w/w-%) NaNO$_3$ in 0.5M NaCl.

TABLE 1

Bottom value, elution volume ($V_e$), top width and symmetry factor as a function of gap width.

| Gap mm | Bottom value (Theoretical plate member) N/m | $V_e$ ml | Top width | Symmetry factor* |
|---|---|---|---|---|
| 0 | 3600 | 3.6 | 2.4 | 10.0 |
| 0.13 | 29400 | 9.0 | 2.1 | 2.7 |
| 0.19 | 29000 | 9.8 | 2.3 | 2.1 |
| 0.25 | 31500 | 10.2 | 2.3 | 2.0 |
| 0.31 | 29500 | 10.3 | 2.4 | 2.4 |
| 0.38 | 28900 | 10.2 | 2.4 | 2.4 |
| 0.50 | 29500 | 10.3 | 2.4 | 2.6 |

*Symmetry factor at 10% of the top height and defined so that the highest symmetry corresponds to 1.

The results shown in the Table illustrate that bottom value, elution volume, top width and symmetry factor are functions of gap width.

We claim:

1. A liquid chromatography column, comprising a column tube including a chromatographic matrix, the matrix being monolithic and porous, liquid flow inlet means and liquid flow outlet means, a distributor located adjacent the inlet for distributing incoming liquid, and, when eluant passes through the matrix, a liquid accommodating gap which is devoid of matrix material, wherein the liquid accommodating gap is between the matrix and the distributor and is directly adjacent the matrix, the gap being effective to improve a theoretical plate number, an elution volume or a symmetry factor of the liquid chromatography column.

2. A column according to claim 1, wherein the gap is smaller than 2 mm.

3. A column according to claim 2, wherein, as the liquid flows through the matrix during chromatography, the counterpressure exerted radially across the matrix is smaller than the counterpressure exerted axially of the matrix in the flow direction.

4. A column according to claim 2, wherein the porosity of the matrix is greater than 2 cm$^3$/g.

5. A column according to claim 1, wherein, as the liquid flows through the matrix during chromatography, the counterpressure exerted radially across the matrix is smaller than the counterpressure exerted axially of the matrix in the flow direction.

6. A column according to claim 5, wherein the porosity of the matrix is greater than 2 cm$^3$/g.

7. A column according to claim 1, wherein the porosity of the matrix is greater than 2 cm$^3$/g.

8. A column according to claim 1, wherein the matrix comprises throughflow pores having a diameter not less than 0.05 $\mu$m and a pore volume greater than 2 cm$^3$/g.

9. A column according to claim 8, wherein the pore volume is in a range of from 5 cm$^3$/g to 30 cm$^3$/g.

10. A column according to claim 1, wherein the gap is present in zero liquid flow conditions.

* * * * *

UNITED STATES PATENT AND TRADEMARK OFFICE
CERTIFICATE OF CORRECTION

PATENT NO. : 5,772,875
DATED : June 30, 1998
INVENTOR(S) : Conny Pettersson et al It is certified that error appears in the above-identified patent and that said Letters Patent is hereby corrected as shown below:

In the Abstract

Line 5, change "is that is" to -- that is--.

Lines 5-6
change "and in that when eluant passes through the matrix" to --and, when eluant passes through the matrix,--.

Signed and Sealed this

Eighth Day of September, 1998

Attest:

BRUCE LEHMAN

Attesting Officer

Commissioner of Patents and Trademarks